US00PP18184P2

(12) United States Plant Patent
Korlipara

(10) Patent No.: US PP18,184 P2
(45) Date of Patent: Nov. 6, 2007

(54) ***COREOPSIS* PLANT NAMED 'AUTUMN BLUSH'**

(50) Latin Name: ***Coreopsis* spp. (*Coreopsis* 'Limerock Ruby' mutant×*Coreopsis auriculata* 'Nana')**
Varietal Denomination: Autumn Blush

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 12 days.

(21) Appl. No.: 11/452,687

(22) Filed: Jun. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct *Coreopsis* plant named 'Autumn Blush' characterized by prolific, bicolor soft yellow and maroon daisy-type flowers on a low mounding plant with linearly lobed leaves.

1 Drawing Sheet

Botanical name: *Coreopsis* spp. (*Coreopsis* 'Limerock Ruby' mutant×*Coreopsis auriculata* 'Nana').
Variety designation: 'Autumn Blush'.

BACKGROUND OF THE INVENTION

The present invention relates to a new and distinct hybrid of *Coreopsis* and given the cultivar name 'Autumn Blush'. *Coreopsis* is in the family Asteraceae. This new cultivar originated from a controlled cross in a cultivated area of *Coreopsis* 'Limerock Ruby' (U.S. Plant Pat. No. 15,455) mutant (a proprietary, unreleased plant) as the seed parent and *Coreopsis auriculata* 'Nana', an unpatented plant, as the pollen parent.

SUMMARY OF THE INVENTION

The following traits have been repeatedly observed and are determined to be the unique characteristics of 'Autumn Blush'. These characteristics in combination distinguish 'Autumn Blush' as a new and distinct cultivar:

1. Large daisy-type flowers that are about 3.5 cm in diameter.
2. Unique soft yellow and maroon bi-colored ray florets.
3. Flower color (ray florets) changes under cool temperatures of spring and fall to a pink blush with a maroon center.
4. Grass green foliage.
5. Very free branching.
6. Very free flowering.
7. Mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a one year old *Coreopsis* 'Autumn Blush' growing in the ground in full sun in the garden in August in Canby, Oreg.

FIG. 2 shows a close up of the early fall flowers showing the color range with cooler temperature.

DETAILED PLANT DESCRIPTION

The following is a detailed description of the new *Coreopsis* cultivar based on observations of a one-year-old specimen grown in the ground in full sun in the trial fields under typical outdoor conditions in August in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 6 to 9.
- *Size.*—70 cm wide and 45 cm tall to top of flowers.
- *Form.*—Mound.
- *Roots.*—Fibrous, Grey Brown, 199D, stems root easily from stem cuttings.

Stem:
- *Type.*—Ascending.
- *Size.*—34 cm tall and 3 mm wide.
- *Internode length.*—5 to 8 cm.
- *Surface.*—Glabrous.
- *Color.*—Deep Green, between Green 137A and Yellow Green 147A.

Leaf:
- *Type.*—Compound, odd pinnate.
- *Shape.*—Ovate, slightly cupped.

*Lobing.*—2 to 5 pinnatifid, linear, each lobe 1 to 2 mm wide and 1 to 3.5 cm long.

*Arrangement.*—Opposite.

*Length including petiole.*—5 to 8 cm, basal leaves can grow to 9.5 cm, leaf size decreases towards stem tip.

*Width.*—3.5 to 4.5 cm.

*Margins.*—Entire.

*Apex.*—Acute.

*Texture.*—Smooth.

*Surface texture.*—Glabrous.

*Venation.*—Pinnate.

*Color.*—Top side — Deep Green, between Green 137A and Yellow Green 147A.

*Bottom.*—Yellow Green 147B.

Inflorescence:

*Type.*—Long stalked terminal heads of daisy type flowers.

*Peduncle description.*—3.5 to 11 cm tall and 1 mm wide, glabrous, Yellow Green 146A.

Flower bud: Round shape, 7 mm wide and 7 mm deep, top half Greyed Orange 163C with the tip Greyed Purple 187A, the bottom half is Yellow Green 148A.

Flower:

*Type.*—Perfect, zygomorphic.

*Size.*—3.5 cm wide and 11 mm deep.

*Ray florets.*—Number: 8. Shape: obovate with the tip three lobed with lobes obtuse and notched and the central lobe the longest, base is quilled with an appendage or lobe which is linear and 4 to 8 mm long and 1 to 1.5 mm wide, margins entire. The ray florets open quilled then flatten out. Size: grows to 19 mm long, 11 mm wide. Texture: soft, velvety, glabrous. Color: Ray floret, topside — Yellow 4B with the bottom ⅓ and edges of the floret Red Purple 59A; in cool temperatures the yellow on the top ⅔ changes to Red 36D. Ray floret, bottom side — Yellow 4A.

*Disc.*—Rounded in overall shape, 11 mm wide and becoming 4 mm deep with maturity, Greyed Orange 163B or C when in bud, opening to Yellow Orange 17B.

*Disc florets.*—7 mm long and 1 mm wide, tubular, entire Orange 22A at the apex to Yellow Orange 13B near base.

*Pistil description.*—On disc florets only, 5 mm long, extruding, 2-branched stigma, Orange 17A.

*Stamen description.*—On disc florets only, 5 in number, filaments less than 2 mm long, Black 202A, pollen sparse, Yellow Orange 17A.

*Bloom period.*—June through September in Canby, Oreg.

*Fragrance.*—Light, Chrysanthemum-like.

Seed: None produced.

*Fertility.*—Infertile.

Disease and pests: *Coreopsis* are susceptible to mildew and fungal spots. No resistance is known for this variety.

COMPARISONS TO SIMILAR *COREOPSIS*

Compared to *Coreopsis auriculata* 'Nana', an unpatented plant and the pollen parent, this new cultivar has similar flower size and petal shape but with narrow leaves and bicolor flowers of light yellow and maroon instead of yellow orange.

Compared to *Coreopsis rosea* 'Sweet Dreams' (U.S. Plant Pat. No. 12,720), this new cultivar has bicolor flowers of light yellow and maroon rather than purple and white. Both are freely branching and flowering with an outwardly spreading habit.

Compared to the seed parent, *Coreopsis rosea* 'Limerock Ruby' mutant, the new cultivar is frost hardy to USDA Zone 6 rather than Zone 10 and has bicolor flowers of light yellow and maroon rather than solid maroon flowers.

I claim:

1. A new and distinct *Coreopsis* plant named 'Autumn Blush' as herein illustrated and described.

* * * * *

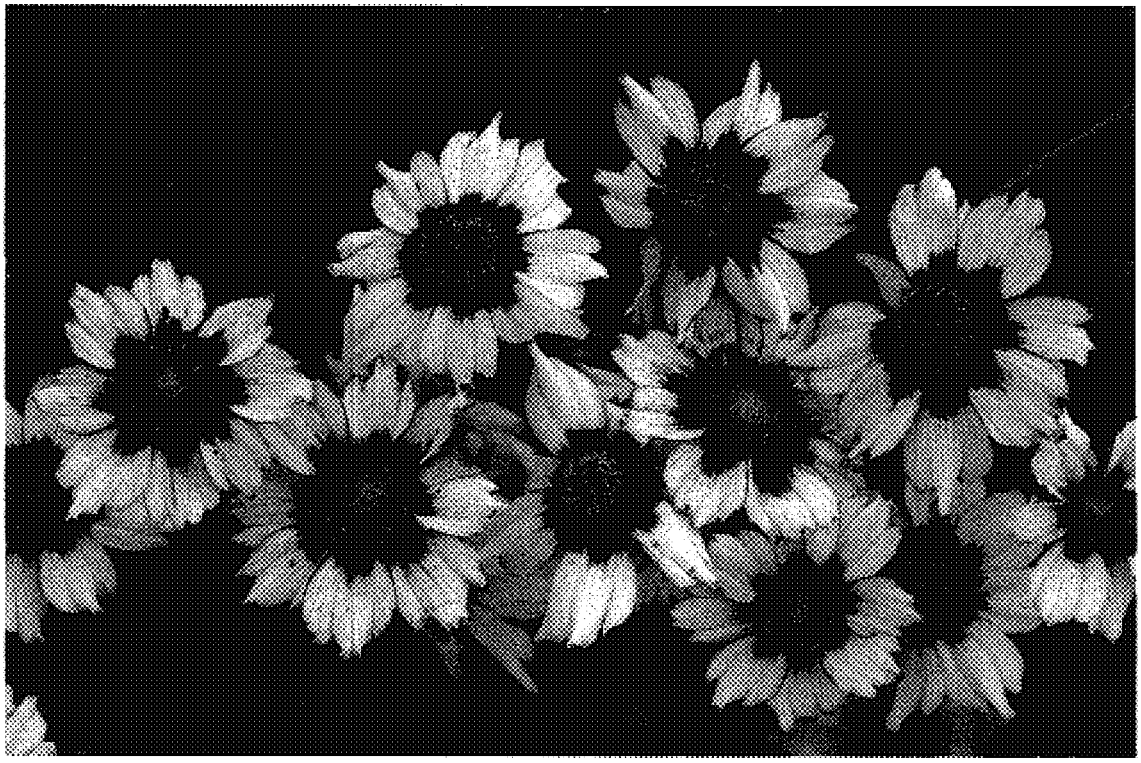

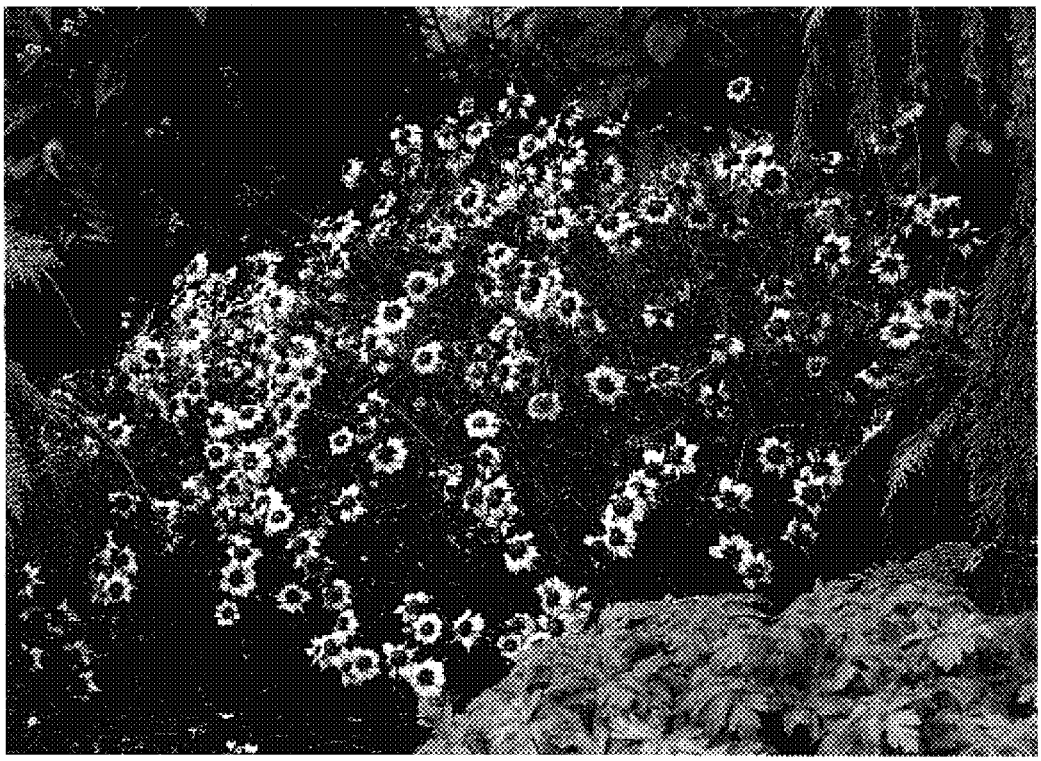
Figure 1 above, Figure 2 below.